US011111055B2

(12) United States Patent
Reece et al.

(10) Patent No.: US 11,111,055 B2
(45) Date of Patent: Sep. 7, 2021

(54) BASKET FOR CARRYING A CONTACT LENS DURING ITS TREATMENT IN A BATH (71) Applicant: Novartis AG, Basel (CH)

(72) Inventors: Daryl Reece, Atlanta, GA (US); Uwe Haken, Norcross, GA (US); Honghui Lu, Johns Creek, GA (US); Oli Jobe, Auburn, GA (US); Alice Weimin Liu, Alpharetta, GA (US)

(73) Assignee: Alcon Inc., Fribourg (CH)

( * ) Notice: Subject to any disclaimer, the term of this patent is extended or adjusted under 35 U.S.C. 154(b) by 71 days.

(21) Appl. No.: 16/216,430

(22) Filed: Dec. 11, 2018

(65) Prior Publication Data
US 2019/0185209 A1 Jun. 20, 2019

Related U.S. Application Data (60) Provisional application No. 62/598,833, filed on Dec. 14, 2017.

(51) Int. Cl.
A61L 12/08 (2006.01)
B65D 21/02 (2006.01)
B29D 11/00 (2006.01)
B08B 3/04 (2006.01)

(52) U.S. Cl.
CPC ........ B65D 21/0206 (2013.01); A61L 12/086 (2013.01); B29D 11/0023 (2013.01); B08B 3/047 (2013.01); B29D 11/0025 (2013.01); B65D 2585/545 (2013.01)

(58) Field of Classification Search
CPC .......... B65D 21/0206; B65D 2585/545; A61L 12/086; B29D 11/0023; B29D 11/0025; B08B 3/047; A45C 11/005
USPC ........................................................ 206/5.1
See application file for complete search history.

(56) References Cited

U.S. PATENT DOCUMENTS

| 3,770,113 | A | * | 11/1973 | Thomas | ............... | A45C 11/005 206/5 |
| 4,200,187 | A | * | 4/1980 | Thomas | ............... | A45C 11/005 134/901 |
| 4,700,729 | A | * | 10/1987 | Thaler | .................. | G02C 13/008 134/139 |
| 4,890,729 | A | * | 1/1990 | Ranalletta | ............ | A45C 11/005 134/901 |
| 5,972,292 | A | * | 10/1999 | DeMeo | ................ | A45C 11/005 134/901 |

(Continued)

Primary Examiner — Steven A. Reynolds
(74) Attorney, Agent, or Firm — Sheng-Hsin Hu (57) ABSTRACT An embodiment of the invention is a basket for holding contact lenses. The basket comprises a first basket and a second basket mating members, each basket member includes a basket wall defining a first cavity, a planar flange extending out around the first cavity, a plurality of spaced fingers extending upward circumferentially from the periphery of the cavity, wherein the first basket and second basket mating members having a same structure, wherein the first basket and second basket mating members forming a second cavity when mated for receiving said contact lens, the cavity inhibiting inversion or rolling over of said contact lens when emplaced therein. A tray that comprises a plurality of baskets is another embodiment of the invention. In addition, the invention provides a stack assembly that comprises a plurality of trays each of which comprises a plurality of baskets.

2 Claims, 10 Drawing Sheets (56) References Cited

U.S. PATENT DOCUMENTS

| | | | | |
|---|---|---|---|---|
| 6,148,992 | A * | 11/2000 | Kanner | A45C 11/005 134/901 |
| 6,719,929 | B2 * | 4/2004 | Winterton | B29C 37/0032 264/1.38 |
| 2003/0024829 | A1 | 2/2003 | Matsuzawa | |
| 2007/0035049 | A1 | 2/2007 | Bruce | |
| 2008/0257389 | A1 | 10/2008 | Daulton | |
| 2012/0279894 | A1 | 11/2012 | Lai | |

* cited by examiner

BASKET FOR CARRYING A CONTACT LENS DURING ITS TREATMENT IN A BATH

This application claims the benefit under 35 USC § 119 (e) of U.S. provisional application No. 62/598,833 filed 14 Dec. 2017, incorporated by reference in its entirety.

BACKGROUND

The present invention provides a basket and a tray for holding contact lenses. The basket and the tray of the present invention is useful in the manufacture of contact lenses involving operations including but not limited to washing, extracting, coating and the like.

Mass production of contact lenses such as soft contact lenses, generally includes one or more bath treatments in which the lenses are treated with water or specific treatment liquids in order to modify the properties of the lenses. For example, in the manufacture of silicone hydrogel soft contact lenses a lens-forming material is dispensed into a mold and is subsequently cured to form the contact lens. After curing any undesirable substances, for example solvents or un-polymerized monomers, contained in the cured contact lens need to be extracted before the contact lens can be worn. In addition, it may be necessary or desirable to apply a coating to the extracted contact lens in order to increase the contact lens' hydrophilic properties. Both, the extraction process as well as the coating process, are typically performed by successively transporting the cured contact lenses through one or more baths.

In this regard, it is known to transport the contact lenses through the baths in the interior of contact lens carriers having the shape of a more or less cylindrical tube having a bottom. The tube and the bottom may comprise openings or slots through which the treatment liquid may enter and exit the interior of the tube to allow the contact lens contained in the interior of the tube to be sufficiently exposed to the treatment liquid. The contact lens is retained in the interior of such tube by means of a circular diaphragm having inwardly extending flexible fins, so that once the contact lens has been inserted into the interior of the tube in the space between the diaphragm and the bottom of the tube, the lens cannot escape from that space until it is removed again from this space, for example with the aid of a suitable gripper. A plurality of such tubes may be arranged side by side and may be transported through the baths. This is an efficient way of treating the lenses in baths, however, only if the duration of exposure of the lens to the treatment liquid or liquids is within certain time limits. In particular, for rather long exposure times as this is the case, for example, in the extraction of silicone hydrogel lenses in solvent or aqueous treatment baths, the efficiency of the treatment process is open to improvement.

Hence, for reasons of efficiency and cost-effectiveness there is a continuing need for contact lens baskets and trays allowing high numbers of contact lenses to be simultaneously exposed to the treatment liquid. On the other hand, it is crucial that the contact lenses are sufficiently exposed to the treatment solvent or liquid as the treatment of the contact lenses, for example the extraction or the coating of the contact lenses, must be as effective and complete as possible without being damaged. At the same time, it is necessary to ensure that the contact lenses cannot escape from their baskets during the bath treatment.

SUMMARY OF THE INVENTION

An embodiment of the present invention is a basket for holding a contact lens, the basket comprises a first basket and a second basket mating members, each basket member comprises a basket wall defining a first cavity, a planar flange extending out around the first cavity, a plurality of spaced fingers extending upward circumferentially from the periphery of the cavity, wherein the first basket and second basket mating members having a same structure, wherein the first basket and second basket mating members forming a second cavity when mated for receiving said contact lens, the cavity inhibiting inversion or rolling over of said contact lens when emplaced therein Another embodiment of the present invention is a tray for holding a plurality of contact lenses and the try comprising a plurality of baskets, wherein each of the basket is capable of holding a contact lens and said basket comprises a first basket and a second basket mating members, each basket member comprises a basket wall defining a first cavity, a planar flange extending out around the first cavity, a plurality of spaced fingers extending upward circumferentially from the periphery of the cavity, wherein the first basket and second basket mating members having a same structure, wherein the first basket and second basket mating members forming a second cavity when mated for receiving said contact lens, the cavity inhibiting inversion or rolling over of said contact lens when emplaced therein.

DESCRIPTION OF THE PREFERRED EMBODIMENTS

The present invention, in one aspect, relates to a basket for holding contact lenses. The basket comprises a first basket and a second basket mating members, each basket member comprises a basket wall defining a first cavity, a planar flange extending out around the first cavity, a plurality of spaced fingers extending upward circumferentially from the periphery of the cavity, wherein the first basket and second basket mating members having a same structure, wherein the first basket and second basket mating members forming a second cavity when mated for receiving said contact lens, the cavity inhibiting inversion or rolling over of said contact lens when emplaced therein.

As used herein, "a basket" refers to an assembly that comprises two basket members and two basket members mated together to form a cavity for receiving a contact lens, all members having openings for allowing fluid to pass through the basket while the contact lens is in place. Preferably, a basket of the present invention comprises a first member and a second member and has a percentage of opening surface over total surface being at least 30%.

Baskets can be made from any easily fabricated material, including, without limitation, plastics, metal, ceramic, glass or similar materials. Preferably, the members of the baskets are made from a plastic material. Examples of suitable plastic materials include polystyrenes, polyolefines, acrylics, polycarbonates, polyacetal resins, polyacrylethers, polyacrylether sulfones, and the like. The most preferred material for the members of a basket is polycarbonate which can be machined or injection molded and can withstand the solvents and washing and coating solution within the temperature range utilized.

The shape and size of a basket is preferably designed to accommodate the shape and size of a contact lens to be held. In a more preferred embodiment of the present invention, the basket for holding a contact lens comprises a pair of mating members (i.e., a first basket member and a second basket member), and the two basket members are mated together to form a cavity for receiving the contact lens. Such cavity inhibits inversion or rolling over of the contact lens when a contact lens is in placed. In an even more preferred embodiment of the invention, the first basket member and the second basket member have a same structure and first basket member the first basket member can be inserted within the second basket member such that there is clearance for a contact lens between the two members, yet not enough so that the contact lens can invert or roll over. In a particularly preferred embodiment, there are through-holes in the centers of the first basket and the second basket members, and 7 to 12 thin lines radiating from the through-holes in the centers of the first basket member and the second basket member and the thin lines have a width less than 3 mm. Preferably, there are 10 to 11 thin lines and the thin lines have a width less than 2 mm to allow maximum flow, to reduce the risk of any less loss during extraction and, but also to provide a minimal surface available for a contact lens to temporarily or permanently contact.

Figure 1:
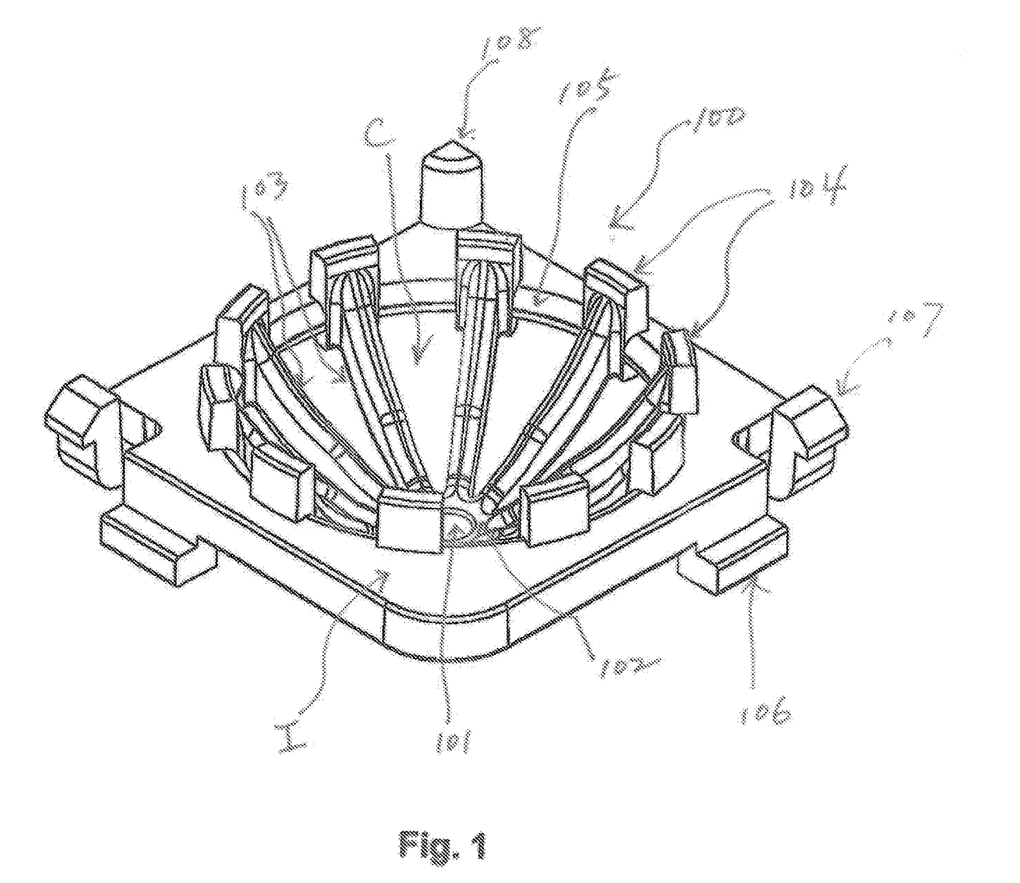
FIG. 1 is an isometric presentation of a basket member for holding a contact lens according to a preferred embodiment of the invention.
Figure 2:
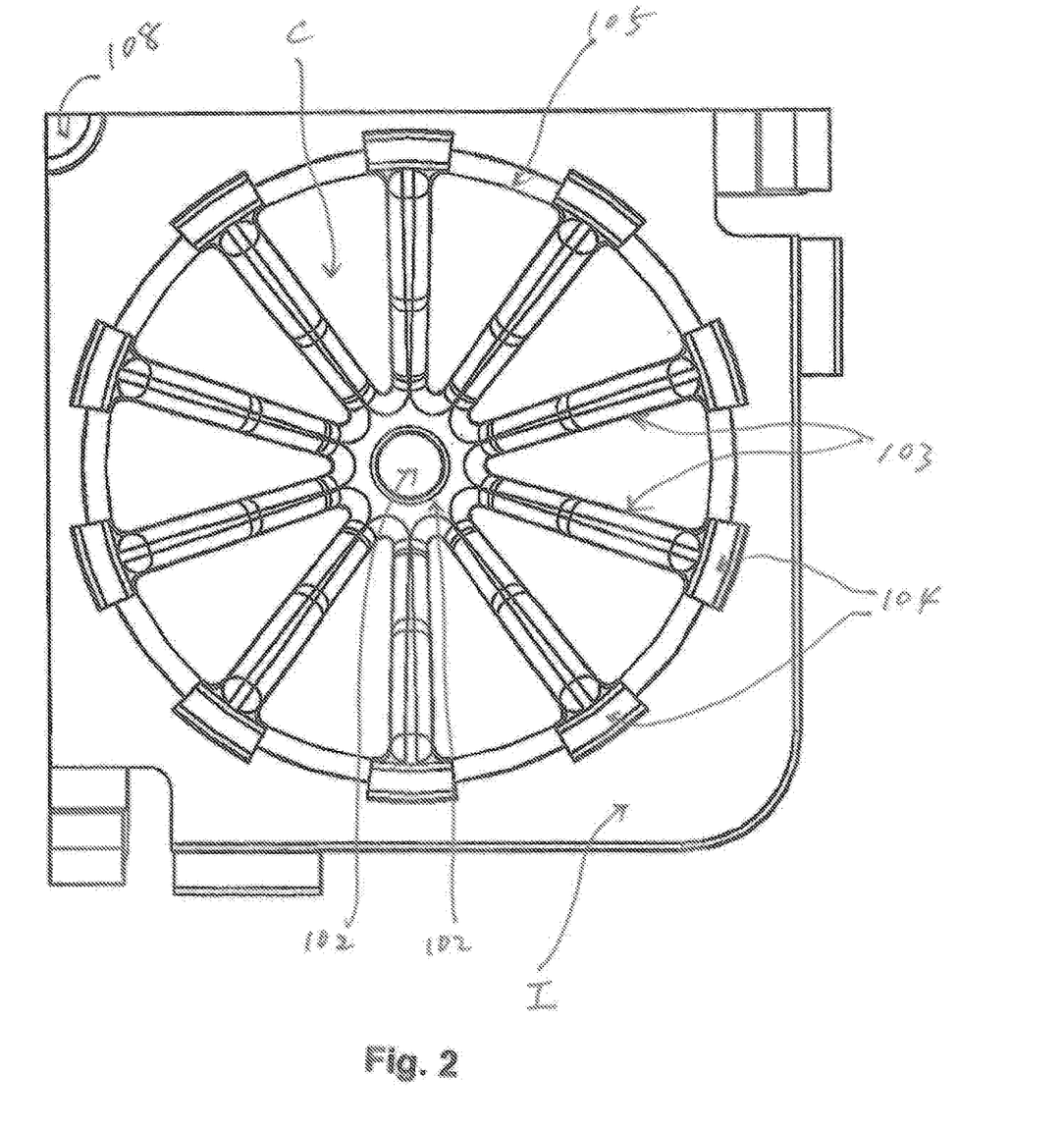
FIG. 2 is a schematic presentation of the bottom view of the basket member
Figure 3:
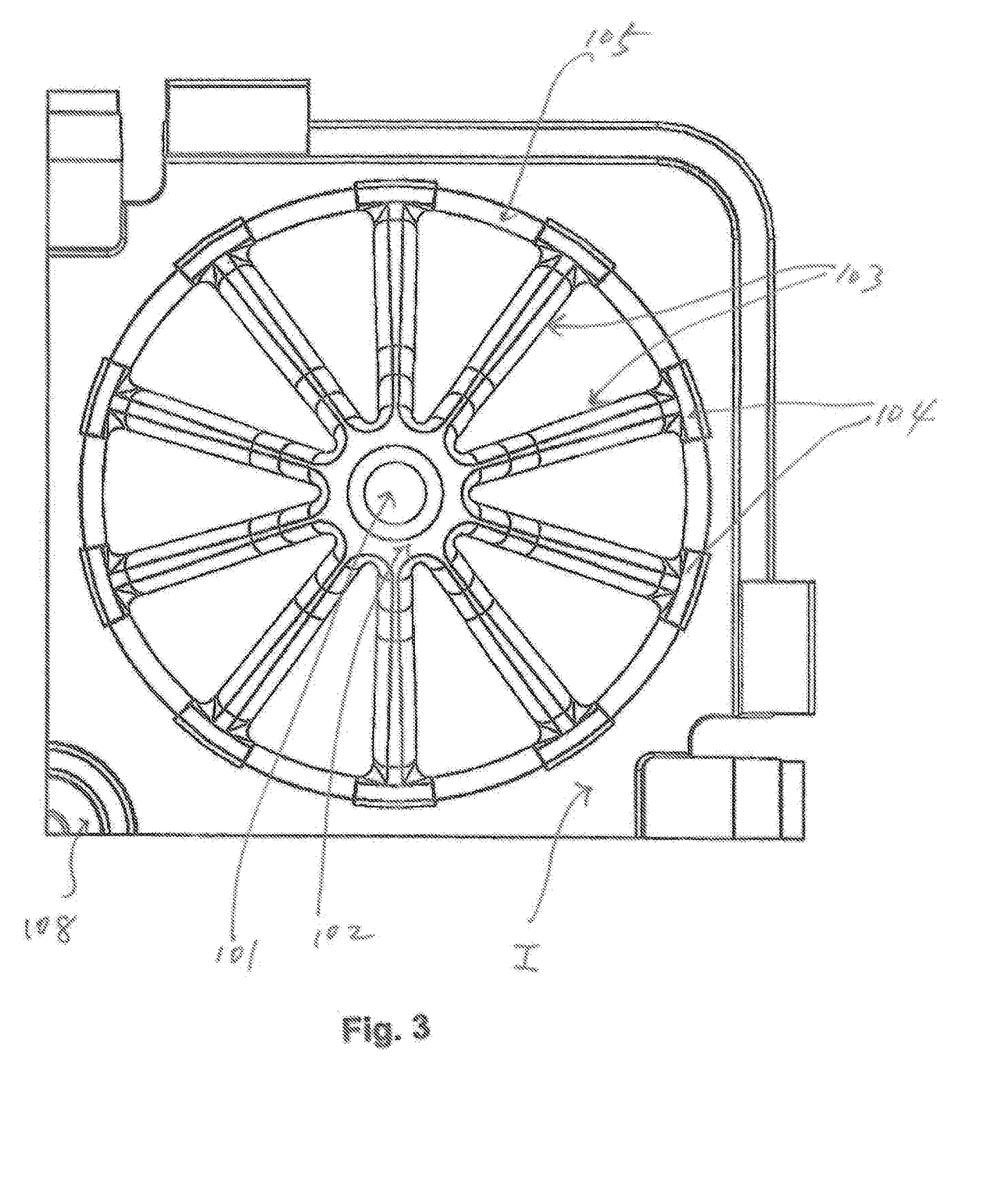
FIG. 3 is a schematic presentation of the top view of the basket member

The cavity of the bucket has a diameter from 15 mm to 30 mm and a depth from 5 mm to 13 mm. The depth of the cavity is measured the perpendicular distance from the planar surface (I) to the lowest point of the inner surface of the cavity (c). The prefer diameter is from 20 mm to 26 mm and a depth of from 8 mm to 13 mm, such that when first basket member the first basket member is inserted within the second basket member to have a clearance for a swollen size of a contact lens when a contact lens in contact with a 100 percent solvent (for example, Isopropyl Alcohol) solution as an extraction medium or in a buffer solution or with a Phosphate-buffered saline (PBS). It is discovered that for a lens swollen in 100% Isopropyl Alcohol in the preferred sized bucket, the optical zone of the centered lens is not touching any parts of the extraction buckets. This can improve lens damage and improve optical quality of the lens. It is also discovered that for the final lens in PBS, this preferred size bucket has two advantages: the upper tray can be removed and the lens stays still in the bottom tray for lens removal and because the lens is centered a higher lens removal rate is expected. FIGS. 1, 2 and 3 represent isometric, bottom and top view, respectfully of the first member of a basket (100) for holding a contact lens according to a preferred embodiment of the invention. The basket comprises a wall defining a first cavity and the basket wall comprises a plurality of thin lines (103) extending from a hub (102) to form a spoke-like configuration to minimize flow restriction for the treatment. The thin lines support a contact lens accommodated in the basket. The basket also comprises an essentially planar flange (I), which extends out around the cavity (C) or surrounds it. The basket further comprises a plurality of spaced fingers (104) extending upward circumferentially around the periphery of cavity (C) or prefer around the rim of cavity (C). Through-hole (101) are cut in the center of the hub, which is also center of first member of the basket. The space between the spaced fingers defines the openings (105). In order to allow as much treatment liquid as possible to flow into and out of the cavity, the open area percentage of the basket wall may be at least 30%, in particular at least 50%, preferably at least 70%, more preferably at least 80%. In addition, a high open area percentage advantageously provides significant material and weight savings. As used herein, the "open area percentage" is defined as the ratio between the total open area and the total (open and non-open) area of the basket wall that defines the cavity of the basket. In other words, the open area percentage is a ratio expressed in percent which reflects how much of the total area of the basket wall is formed by passageways or open areas or perforations.

Figure 4:
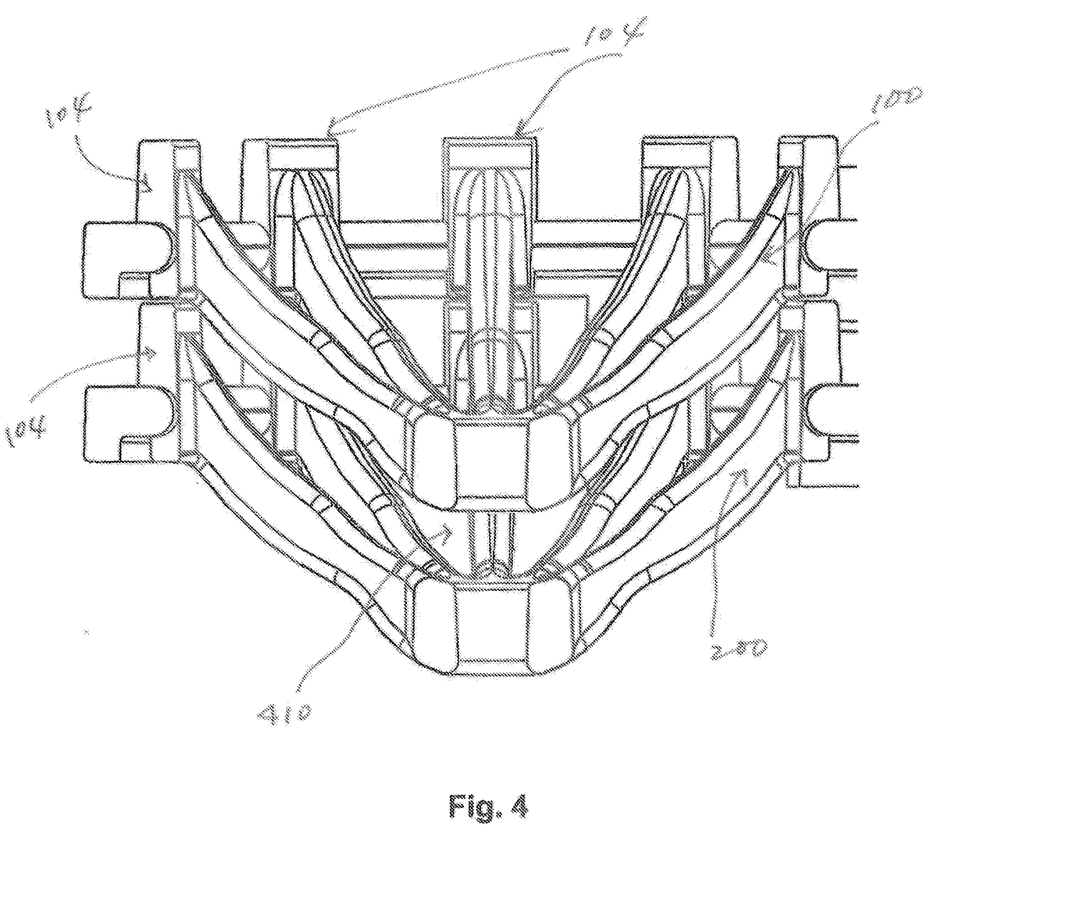
FIG. 4 is a cutaway view of a basket according to a preferred embodiment of the invention.

Referring to FIG. 4, a cavity (410) formed by mating the first basket member (100) and the second basket member (200). The first basket member (100) and the second basket member (200) have the same structure. According to the invention, mating refers to insert the first basket member (100) into the second basket member to have a convex surface of the first basket member facing the concave surface of the second basket member and form a second cavity (410). The second cavity (410) has clearance for a lens between the two members, but not enough for the lens to invert or roll over when the lens is place therein.

In addition to the benefits of using the basket of the invention mentioned earlier, addition advantage of using a basket of the invention is that the basket is very simple to construct because the first basket member and the second basket member have the same structure. The basket is stackable which enable high lens package for treatment in a bath. In addition, the adhesion of a contact lens to any part of the basket can be minimized and/or eliminated probably because there is not sufficient surface area with which a lens could maintain a permanent contact. By using baskets of the invention, contact lenses can be treated uniformly during a manufacturing process such as washing, extracting, coating, drying and the like.

The present invention, in another aspect, relates to a tray for holding a plurality of contact lenses. A tray of the invention is useful for carrying out a process, such as washing, extracting, coating, drying and the like on batches containing a plurality of contact lenses. Thus, the efficiency and productivity of the processing of contact lenses, can be substantially enhanced by using trays of the invention.

"A tray" as used herein refers to an assembly holding a plurality of baskets. A plurality of baskets can be intrinsic parts of a tray, or can be assembled together by stacking a first basket member on the top of the second basket member with or without support members. "Support members" means any structural elements, for example, a metal frame, which together can hold a plurality of baskets. A plurality of baskets can be arranged in any way, for example, in rows or a matrix, in a tray.

Preferably, a tray of the invention comprises a first tray portion which holds the first members of a plurality of baskets, a second tray portion which holds the second members of the plurality of basket. Each of the first members can be inserted within one second member such that there is clearance for a contact lens between the two members, yet not enough so that the contact lens can invert or roll over when emplaced therein.

Trays of invention can be made from any easily fabricated material, including, without limitation, plastics, metal, ceramic, glass or similar materials, preferably from a plastic material. Examples of suitable plastic materials include polystyrenes, polyolefines (for example, polypropylene), acrylics, polycarbonates, polyacetal resins, polyacrylethers, polyacrylether sulfones, and the like.

Figure 5:
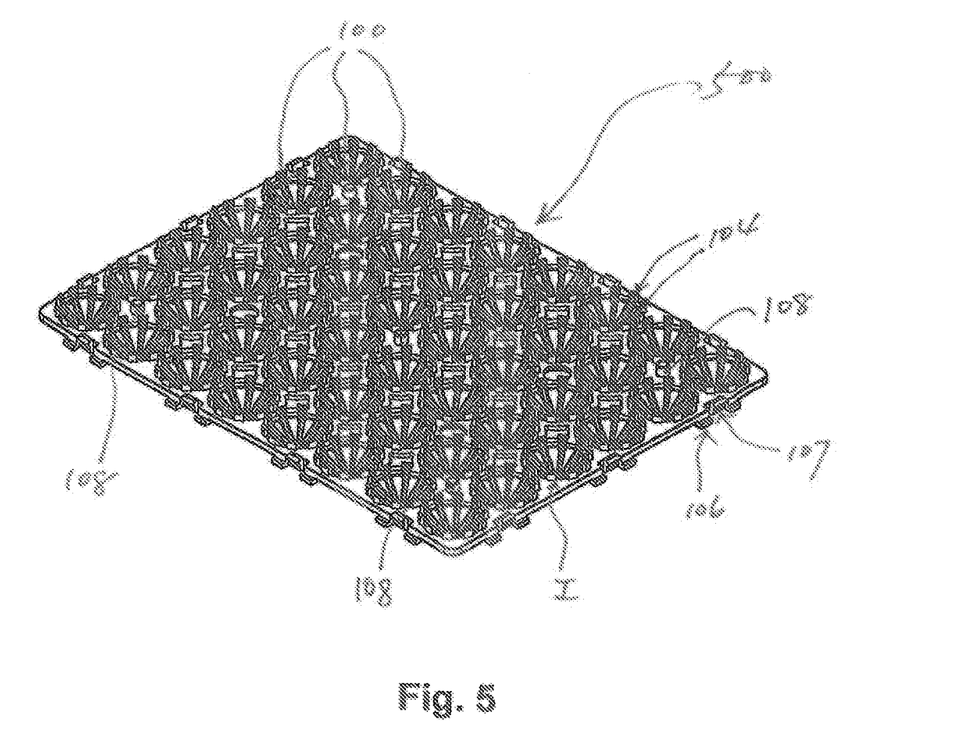
FIGS. 5 and 6 are an isometric view of a portion of a first portion of tray and a second portion of tray, respectfully, containing a plurality of the basket members according to a preferred embodiment of the invention.
Figure 6:
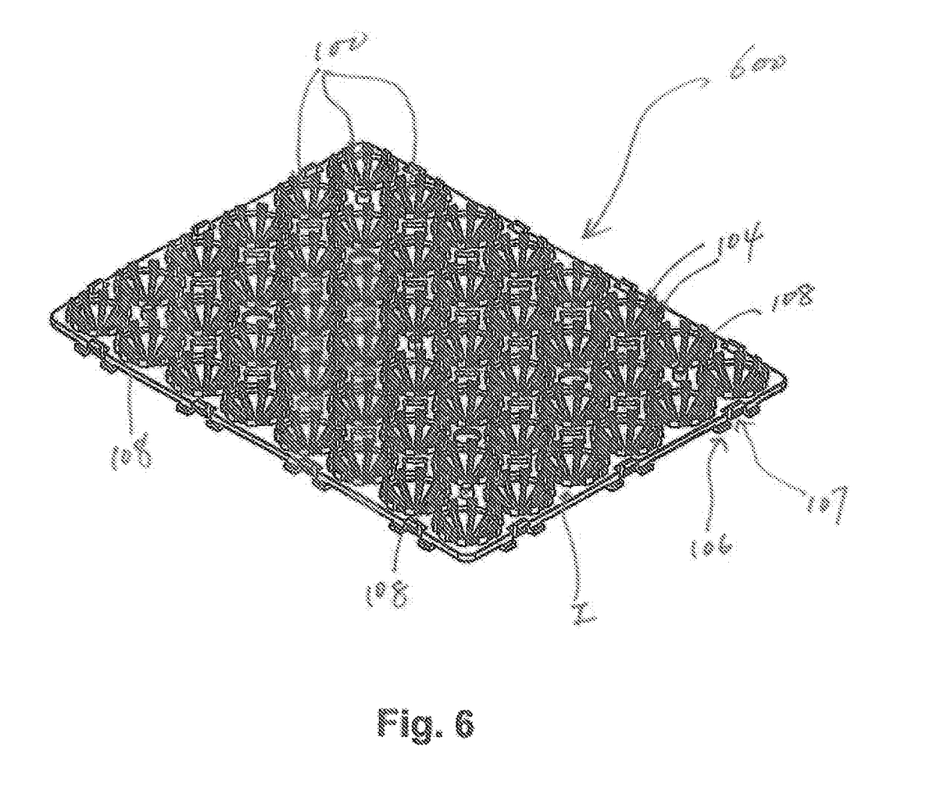

FIGS. 5-6 schematically illustrate the isometric view of a first tray portion and a second tray portion, respectfully, for holding contact lenses according to a preferred embodiment of the invention. A plurality of first basket members (100) are integrally formed with the planar substrate into a first tray portion (500). A plurality of second basket members (200) are integrally formed with the planar substrate into a second tray portion (600). The substrate is made from the same material as for baskets. The material can be any easily fabricated material, including, without limitation, plastics, metal, ceramic, glass or similar materials. Preferably, the members of the baskets are made from a plastic material. Examples of suitable plastic materials include polystyrenes, polyolefines such as polypropylene, acrylics, polycarbonates, polyacetal resins, polyacrylethers, polyacrylether sulfones, and the like. The first tray portion and the second tray portion have a same structure.

The first tray portion (500) comprises a plurality of first basket members (100) with its spaced fingers (104). As an example, FIGS. 5-6 illustrate the first tray portion (500) and second tray portion (600), respectfully, each has 48 buckets (6×8) and comprises a plurality of top laches (107) and bottom laches (106) along the four edges of the each tray portion which can be snapped to attach to a support element, for example a metal frame. The each tray portion further comprises a plurality of nested posts (108) which has a hollow structure, i.e. each nested post has solid surface viewed from the top, but has a hole passage viewed from the other side (bottom). Here, top and bottom is a relative term only and is not absolute position. These nested posts (108) allow the first tray portion (500) stack onto the second tray portion (600) by inserting the nested post (108) of the second tray portion (600) into the hole passage of the nested post (108) of the first tray portion (500) to form a tray. As described before, the first tray portion and the second tray portion have the same structure, just like first bucket member and the second bucket member have the same structure. The spaced fingers (104) of the second bucket member serves as spacing members which position the first tray portion relative to the second tray portion. The nested posts (108) serves as alignment elements which keep the first tray portion and the second tray portion are aligned with each other when stacked together, therefore the nested posts (108) keep both tray portions are fixed in X and Y directions. Here, stacking between the two refers to insert the first tray portion (500) into the second tray portion to have a convex surface of the plurality first basket members on the first tray portion facing the concave surface of the plurality second basket members on the second tray portion and form a plurality of second cavity (410). The second cavity (410) has clearance for a lens between the two members, but not enough for the lens to invert or roll over when the lens is place therein.

Figure 7:
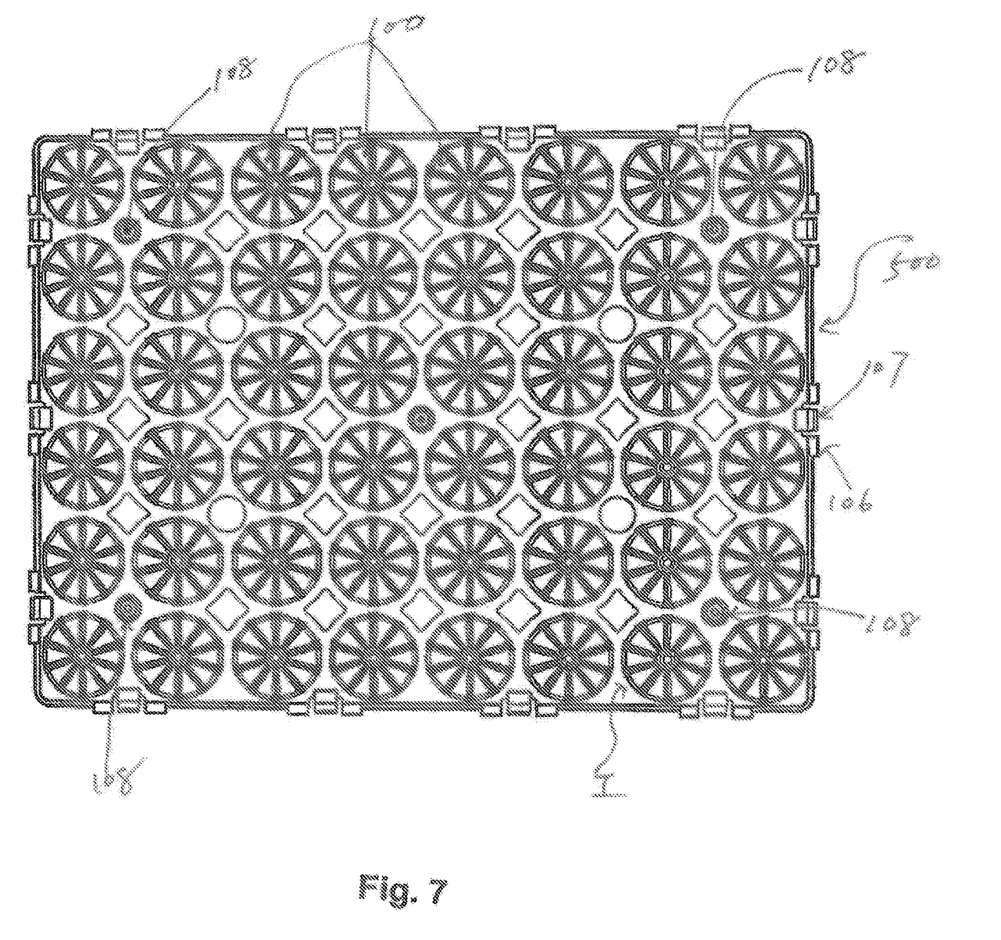
FIGS. 7 and 8 are a schematic presentation of bottom view of a first portion of tray and a second portion of tray, respectfully, containing a member of basket members according to a preferred embodiment of the invention.
Figure 8:
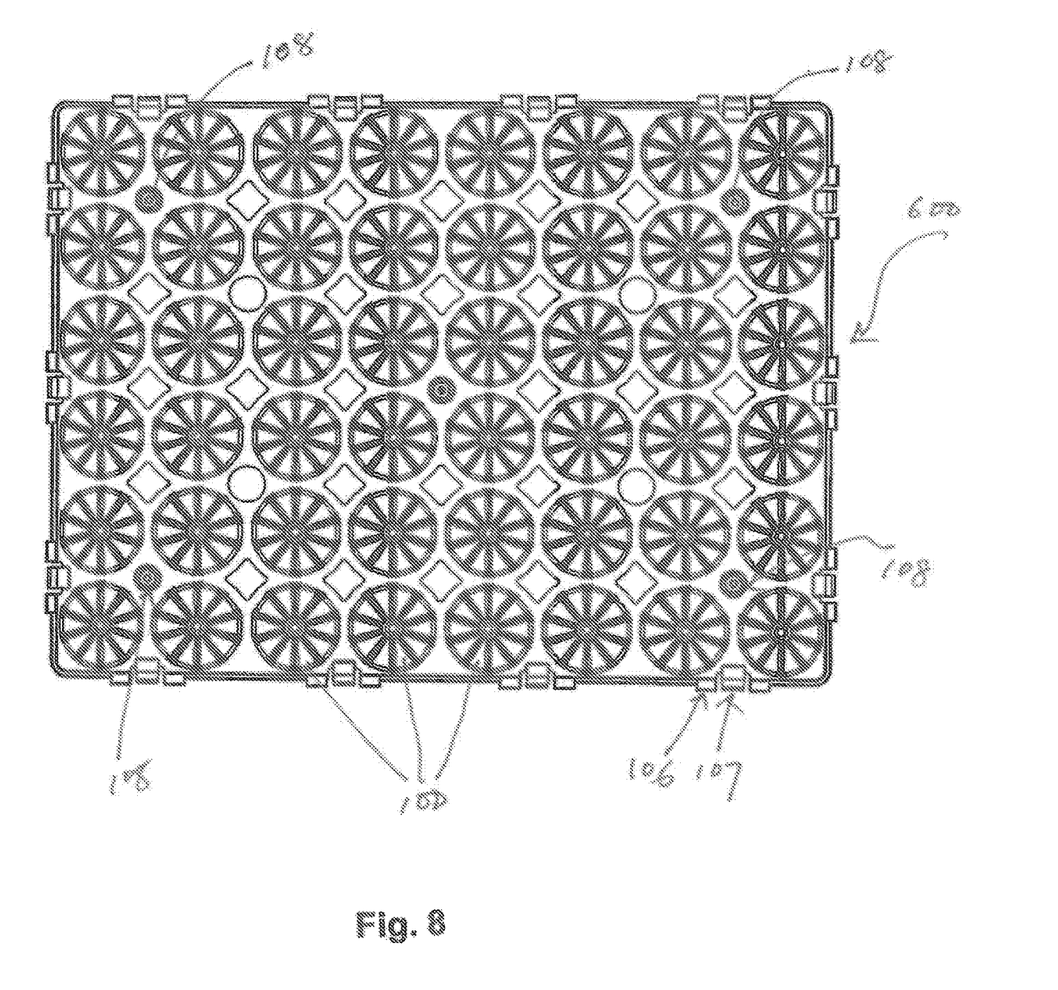

FIGS. 7 and 8 schematically illustrate the bottom view of the first tray portion and the second tray portion, respectfully.

Figure 9:
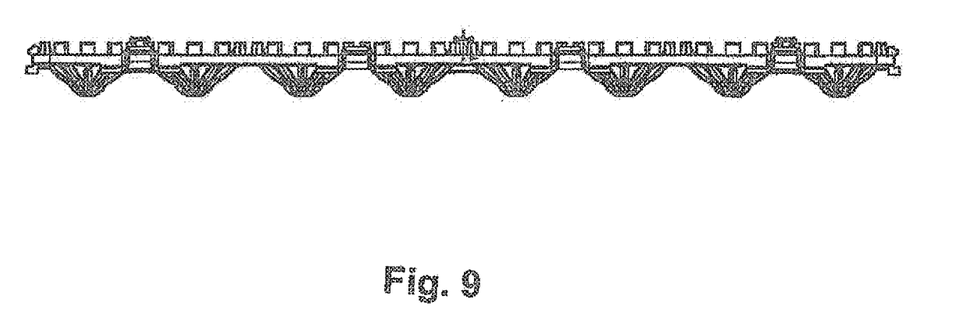
FIG. 9 is a schematic presentation of a front view of portion of a first portion of tray or a second portion of tray, containing a member of basket members according to a preferred embodiment of the invention.

FIG. 9 is a schematic presentation of a front view of portion of a first portion of tray or a second portion of tray, containing a member of basket members according to a preferred embodiment of the invention.

Figure 10:
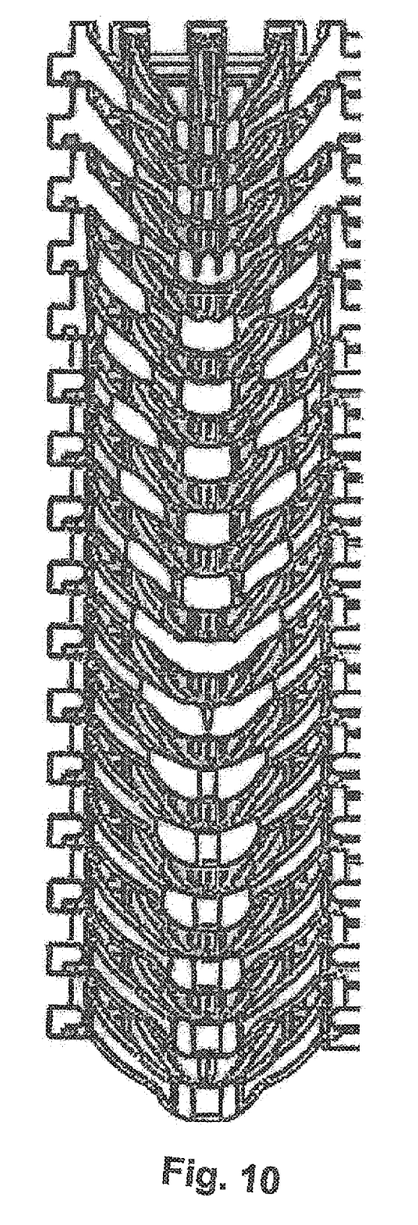
FIG. 10 is a schematic presentation of a front view of a cross section of stack of baskets according to a preferred embodiment of the invention.

The present invention, in still another aspect, relates to a stack assembly for holding contact lenses. The stack assembly of the invention comprises two or more trays of the invention and a stacking means for stacking together the trays. FIG. 10 illustrates a front cross section view of a stack assemble of for holding contact lenses. By using a stack assembly of the invention, large numbers of contact lenses can be processed simultaneously in a manufacturing process such as washing, extracting, coating, drying and the like, resulting high though-put efficiency of the manufacturing process.

What is claimed is:

1. A basket for holding a contact lens, the basket comprises a first basket and a second basket mating members, each basket member comprises a basket wall defining a first cavity, a planar flange extending out around the first cavity, a plurality of spaced fingers extending upward circumferentially from the periphery of the first cavity, wherein the first basket and second basket mating members having a same shape, wherein there are through-holes in the center of the first basket and the second basket mating members, wherein the first basket member has a convex surface which faces a concave surface of the second basket member, wherein the first basket and second basket members are mated with one another so that the convex surface is inserted into the concave surface to form a second cavity for receiving said contact lens, the second cavity inhibiting inversion or rolling over of said contact lens when emplaced therein.

2. The basket of claim 1, wherein the basket wall comprises a plurality of thin lines extending from a hub to form a spoke-like configuration to minimize flow restriction for the treatment.

\* \* \* \* \*